US008360984B2

(12) United States Patent
Yadav et al.

(10) Patent No.: US 8,360,984 B2
(45) Date of Patent: Jan. 29, 2013

(54) HYPERTENSION SYSTEM AND METHOD (75) Inventors: Jay Yadav, Atlanta, GA (US); Michael G. Ellis, Alpharetta, GA (US)

(73) Assignee: CardioMEMS, Inc., Atlanta, GA (US)

( * ) Notice: Subject to any disclaimer, the term of this patent is extended or adjusted under 35 U.S.C. 154(b) by 264 days.

(21) Appl. No.: 12/321,904

(22) Filed: Jan. 27, 2009

(65) Prior Publication Data

US 2010/0262021 A1 Oct. 14, 2010

Related U.S. Application Data (60) Provisional application No. 61/062,601, filed on Jan. 28, 2008.

(51) Int. Cl.
*A61B 5/0215* (2006.01)
*A61B 5/021* (2006.01)
*A61B 5/03* (2006.01)

(52) U.S. Cl. ......... 600/488; 600/505; 600/486; 600/561
(58) Field of Classification Search .................. None
See application file for complete search history.

(56) References Cited

U.S. PATENT DOCUMENTS

| | | | |
|---|---|---|---|
| 5,117,835 A * | 6/1992 | Mick | 600/561 |
| 5,296,730 A | 3/1994 | Takano | 257/417 |
| 5,668,033 A | 9/1997 | Ohara | 999/51 |
| 6,011,607 A | 1/2000 | Yamazaki | 349/153 |
| 6,015,386 A * | 1/2000 | Kensey et al. | 600/486 |
| 6,020,257 A | 2/2000 | Leedy | 438/626 |
| 6,025,725 A | 2/2000 | Gershenfeld | 324/652 |
| 6,111,520 A | 8/2000 | Allen | 340/870.16 |
| 6,264,601 B1 | 7/2001 | Jassawalla | 600/16 |
| 6,278,379 B1 | 8/2001 | Allen | 340/870.16 |
| 6,329,696 B1 | 12/2001 | Tanaka | 257/419 |
| 6,855,115 B2 | 2/2005 | Fonseca | 600/488 |
| 7,020,508 B2 * | 3/2006 | Stivoric et al. | 600/390 |
| 7,038,470 B1 | 5/2006 | Johnson | 324/664 |
| 7,147,604 B1 | 12/2006 | Allen | 600/549 |
| 7,245,117 B1 | 7/2007 | Joy | 324/76.53 |
| 7,353,711 B2 | 4/2008 | O'Dowd | 73/718 |
| 7,574,792 B2 | 8/2009 | O'Brien | 29/606 |
| 7,621,036 B2 | 11/2009 | Cros | 29/595 |
| 7,647,836 B2 | 1/2010 | O'Brien | 73/756 |
| 7,662,653 B2 | 2/2010 | O'Brien | 438/51 |
| 7,699,059 B2 | 4/2010 | Fonseca | 128/899 |
| 8,025,625 B2 | 9/2011 | Allen | 600/561 |
| 2003/0045772 A1 | 3/2003 | Reich | 600/17 |
| 2004/0022640 A1 | 2/2004 | Siess | 73/1.59 |
| 2004/0049363 A1 | 3/2004 | Shimizu | 702/139 |
| 2004/0079941 A1 | 4/2004 | Yamazaki | 438/455 |
| 2004/0147803 A1 | 7/2004 | Hegde | 600/16 |
| 2004/0193058 A1 | 9/2004 | Montegrande et al. | |
| 2005/0187482 A1 | 8/2005 | O'Brien | 600/486 |
| 2005/0228298 A1 | 10/2005 | Banet et al. | |
| 2006/0122517 A1 | 6/2006 | Banet et al. | |
| 2006/0174712 A1 | 8/2006 | O'Brien | 73/756 |
| 2006/0287602 A1 | 12/2006 | O'Brien | 600/485 |
| 2007/0158769 A1 | 7/2007 | You | 257/415 |
| 2008/0154101 A1 | 6/2008 | Jain et al. | |
| 2010/0121133 A1 | 5/2010 | Schumer | 600/17 |

FOREIGN PATENT DOCUMENTS

| | | |
|---|---|---|
| AU | 2010208298 | 5/2010 |
| CA | 2750647 | 5/2010 |
| EP | 2391263 | 5/2010 |
| MX | a/2011/007966 | 5/2010 |
| WO | WO 2007/047571 | 4/2007 |
| WO | WO 2010/088279 | 5/2010 |

OTHER PUBLICATIONS

International Search Report and Written Opinion for International Application No. PCT/US2010/022243 (mailed Dec. 7, 2010).
International Preliminary Report on Patentability issued on Aug. 2, 2011 by the International Bureau for International Application No. PCT/US2010/022243 (Applicant—CardioMems, Inc. // Inventor—Yadev) (6 pages).
International Search Report issued on Apr. 24, 2007 by the International Searching Authority for International Application No. PCT/US2006/040352 (Applicant—CardioMems, Inc. // Inventor—You) (2 pages).
Written Opinion issued on Apr. 24, 2007 by the International Searching Authority for International Application No. PCT/US2006/040352 (Applicant—CardioMems, Inc. // Inventor—You) (5 pages).
International Preliminary Report on Patentability issued on Apr. 16, 2008 by the International Bureau for International Application No. PCT/US2006/040352 (Applicant—CardioMems, Inc. // Inventor—You) (6 pages).
Requirement for Restriction/Election issued Jun. 18, 2008 by the USPTO for U.S. Appl. No. 11/546,852, filed Oct. 12, 2006 (Inventor—You) (7 pages).
Notice of Abandonment issued Feb. 9, 2009 by the USPTO for U.S. Appl. No. 11/546,852, filed Oct. 12, 2006 (Inventor—You) (2 pages).
Response to Restriction Requirement filed Feb. 9, 2010 at the USPTO for U.S. Appl. No. 11/546,852, filed Oct. 12, 2006 (Inventor—You) (2 pages).
Petition for Review filed Feb. 9, 2010 at the USPTO for U.S. Appl. No. 11/546,852, filed Oct. 12, 2006 (Inventor—You) (2 pages).
Petition Decision issued Apr. 14, 2010 by the USPTO for U.S. Appl. No. 11/546,852, filed Oct. 12, 2006 (Inventor—You) (2 pages).
Non-final Rejection issued Jun. 21, 2010 by the USPTO for U.S. Appl. No. 11/546,852, filed Oct. 12, 2006 (Inventor—You) (13 pages).
Response to Non-final Rejection filed Dec. 21, 2010 at the USPTO for U.S. Appl. No. 11/546,852, filed Oct. 12, 2006 (Inventor—You) (11 pages).
Final Rejection issued Mar. 3, 2011 by the USPTO for U.S. Appl. No. 11/546,852, filed Oct. 12, 2006 (Inventor—You) (14 pages).

(Continued)

*Primary Examiner* — Shafiqul Haq
(74) *Attorney, Agent, or Firm* — Ballard Spahr LLP (57) ABSTRACT

Disclosed are hypertension systems and related methods that include a blood pressure sensor located or implanted under the skin of a patient, and electronics, which may have the size and shape of a wrist watch, for example, that monitors the blood pressure of the patient by communicating with the implanted sensor.

20 Claims, 4 Drawing Sheets

OTHER PUBLICATIONS

Amendment submitted with Request for Continued Examination on Sep. 6, 2011 at the USPTO for U.S. Appl. No. 11/546,852, filed Oct. 12, 2006 (Inventor—You) (13 pages).

Non-final Rejection issued Nov. 30, 2011 by the USPTO for U.S. Appl. No. 11/546,852, filed Oct. 12, 2006 (Inventor—You) (17 pages).

Non-final Rejection issued Mar. 28, 2011 by the USPTO for U.S. Appl. No. 12/291,201, filed Nov. 7, 2008 (Inventor—Schumer) (8 pages).

Response to Non-final Rejection filed Sep. 28, 2011 at the USPTO for U.S. Appl. No. 12/291,201, filed Nov. 7, 2008 (Inventor—Schumer) (14 pages).

Final Rejection issued Dec. 14, 2011 by the USPTO for U.S. Appl. No. 12/291,201, filed Nov. 7, 2008 (Inventor—Schumer) (10 pages).

Claims Amendment filed Mar. 8, 2012 with the European Patent Office for European Patent Application No. 10736346.7, filed Jan. 27, 2010 (Applicant—CardioMems, Inc. // Inventor—Yadev) (7 pages).

* cited by examiner

HYPERTENSION SYSTEM AND METHOD

This application claims the benefit of U.S. Provisional Application No. 61/062,601, filed Jan. 28, 2008.

BACKGROUND OF THE INVENTION

The present invention relates to hypertension systems and methods, and more particularly, to a wireless blood pressure monitoring system and method embodying an implantable blood pressure sensor that is implanted under the skin of a patient, and portable sensing electronics that monitors the blood pressure of the patient.

Over the past 20 years, advances in the field of microelectronics have enabled the realization of microelectromechanical systems (MEMS) and corresponding batch fabrication techniques. These developments have allowed the creation of sensors and actuators with micrometer-scale features. With the advent of the above-described capability, heretofore implausible applications for sensors and actuators are now significantly closer to commercial realization.

In parallel, much work has been done in the development of pressure sensors. Pressure sensors are disclosed, for example, in U.S. Pat. No. 6,855,115, issued Feb. 15, 2005; U.S. patent application Ser. No. 10/054,671, filed Jan. 22, 2002; U.S. patent application Ser. No. 10/215,377, filed Aug. 7, 2002; U.S. patent application Ser. No. 10/215,379, filed Aug. 7, 2002; U.S. patent application Ser. No. 10/943,772, filed Sep. 16, 2004; U.S. patent application Ser. No. 11/157,375, filed Jun. 21, 2005; U.S. patent application Ser. No. 11/314,696 filed Dec. 20, 2005, and U.S. patent application Ser. No. 11/402,439 filed Apr. 12, 2006 all of which are incorporated herein by reference.

In particular, absolute pressure sensors, in which the pressure external to the sensor is read with respect to an internal pressure reference, are of interest. The internal pressure reference is a volume within the sensor, sealed, which typically contains a number of moles of gas (the number can also be zero, i.e. the pressure reference can be a vacuum, which can be of interest to reduce temperature sensitivity of the pressure reference as known in the art). The external pressure is then read relative to this constant and known internal pressure reference, resulting in measurement of the external absolute pressure. For stability of the pressure reference and assuming the temperature and volume of the reference are invariant or substantially invariant, it is desirable that the number of moles of fluid inside the reference does not change. One method to approach this condition is for the reference volume to be hermetic.

The term hermetic is generally defined as meaning "being airtight or impervious to air." In reality, however, all materials are, to a greater or lesser extent, permeable, and hence specifications must define acceptable levels of hermeticity. An acceptable level of hermeticity is therefore a rate of fluid ingress or egress that changes the pressure in the internal reference volume (a.k.a. pressure chamber) by an amount preferably less than 10 percent of the external pressure being sensed, more preferably less than 5 percent, and most preferably less than 1 percent over the accumulated time over which the measurements will be taken. In many biological applications, an acceptable pressure change in the pressure chamber is on the order of 0.5-5 mm Hg/year.

The pressure reference is typically interfaced with a sensing means that can sense deflections of boundaries of the'pressure reference when the pressure external to the reference changes. A typical example would be bounding at least one side of the pressure reference with a deflectable diaphragm or plate and measuring the deflection of the diaphragm or plate by use of, among other techniques, a piezoresistive or a capacitance measurement. If the deflection of the diaphragm or plate is sufficiently small, the volume change of the pressure reference does not substantially offset the pressure in the pressure reference.

Such pressure sensors may be made of materials and be constructed in a manner that allow them to be implanted within a person's body. It would be desirable to take advantage of this capability to provide for an implantable blood pressure sensor. It would be desirable to have hypertension systems and methods that allow real-time remote monitoring of a patient's blood pressure.

BRIEF DESCRIPTION OF THE DRAWINGS

The various features and advantages of the present invention may be more readily understood with reference to the following detailed description taken in conjunction with the accompanying drawings, wherein like reference numerals designate like structural elements, and in which:

FIG. 4 illustrates yet another implementation of the; and

DETAILED DESCRIPTION OF THE INVENTION

Figure 1:
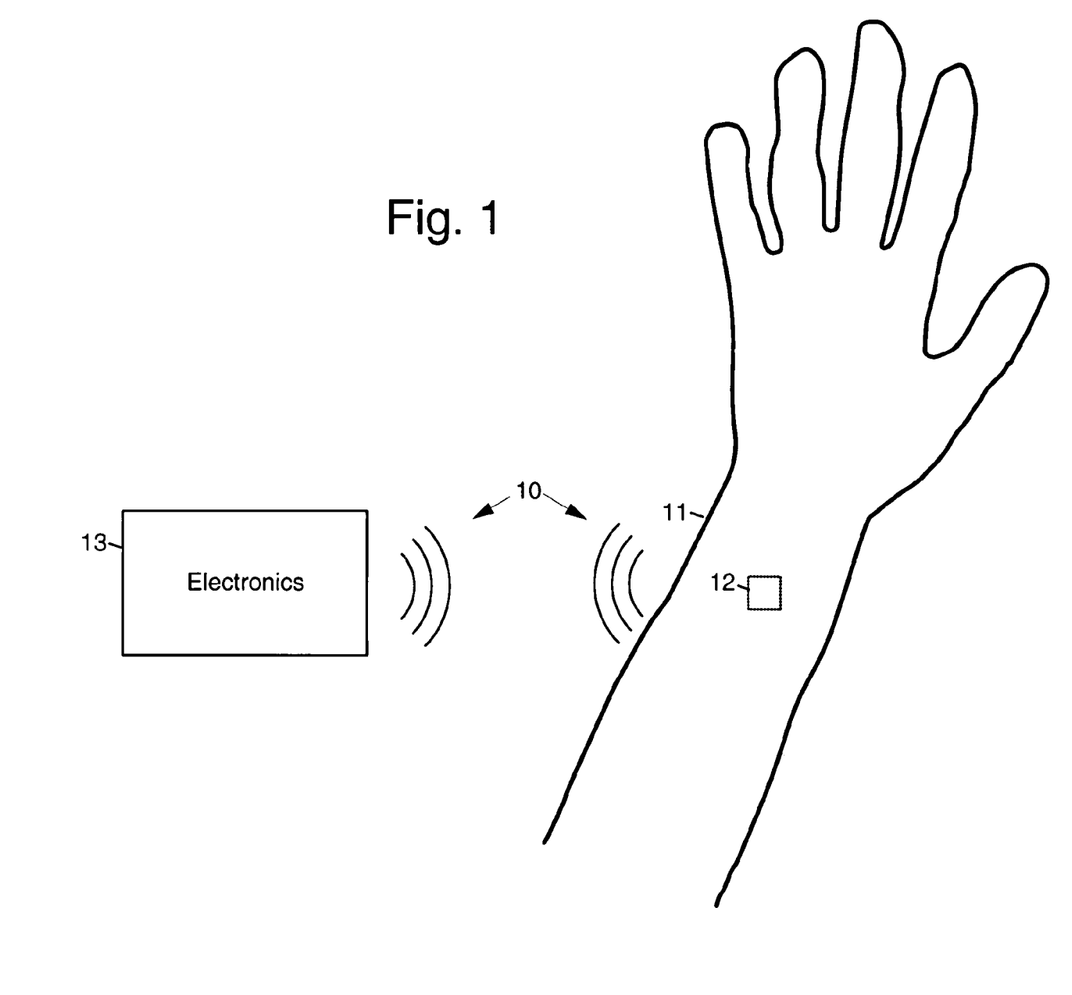
FIG. 1 illustrates an exemplary hypertension system.

Referring now to the drawing figures, disclosed are hypertension systems 10 that include an implantable blood pressure sensor 12 that may be located beneath the skin of a wrist 11 of a patient, and wireless monitoring electronics 13, which may have the size and shape of a wrist watch, for example, that wirelessly monitors and records the blood pressure of the patient. An exemplary basic hypertension system 10 is shown in FIG. 1. Details of exemplary hypertension systems 10 are shown in FIGS. 2-5.

As is shown in FIG. 1, an exemplary hypertension system 10 comprises an implantable inductive-capacitive (LC) sensor 12 that is implanted in the wrist of a patient to monitor the patient's blood pressure. The sensor 12 may be implanted in or around the brachial or radial arteries in the patients arm. Appropriate blood pressure readings may readily be obtained in and in the vicinity of these locations. The sensor 12 is configured to resonate at a frequency corresponding to the blood pressure, at any given instance. An external wireless electronics unit 13 (wireless monitoring electronics 13) wirelessly interrogates the resonant frequency of the implanted sensor 12. The resonant frequency output by the sensor 12 corresponds to the blood pressure of the patient.

The electronics unit 13, or wireless monitoring electronics 13, may be implemented as a miniaturized one port network analyzer 13, embodied in a wrist watch, for example. The wrist watch type network analyzer 13 is dedicated to blood pressure measurements by sitting adjacent to, and constantly reading, the resonant frequency of the implanted LC sensor 12 inside the wrist 11 of the patient.

Figure 2:
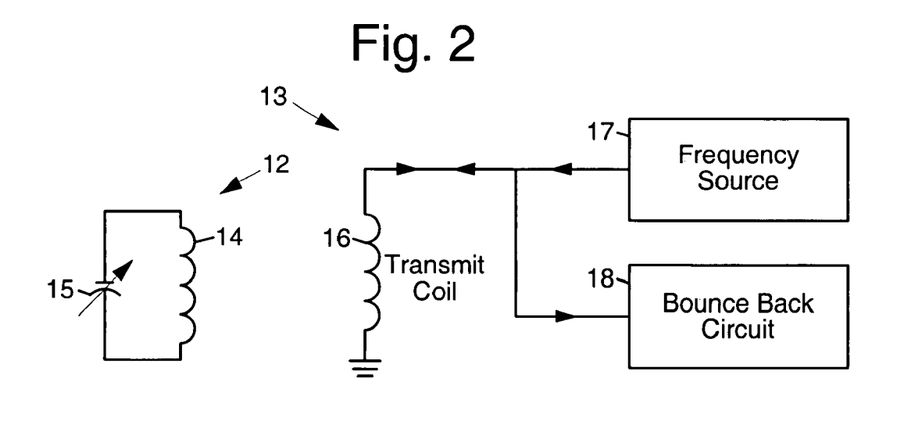
FIG. 2 illustrates one implementation of the hypertension system.
Figure 3:
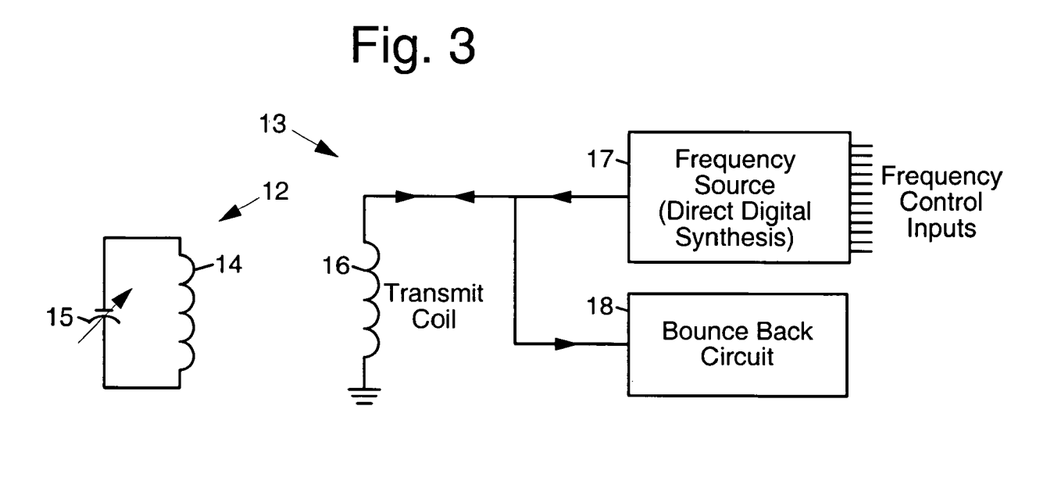
FIG. 3 illustrates another implementation of the hypertension system.
Figure 4:
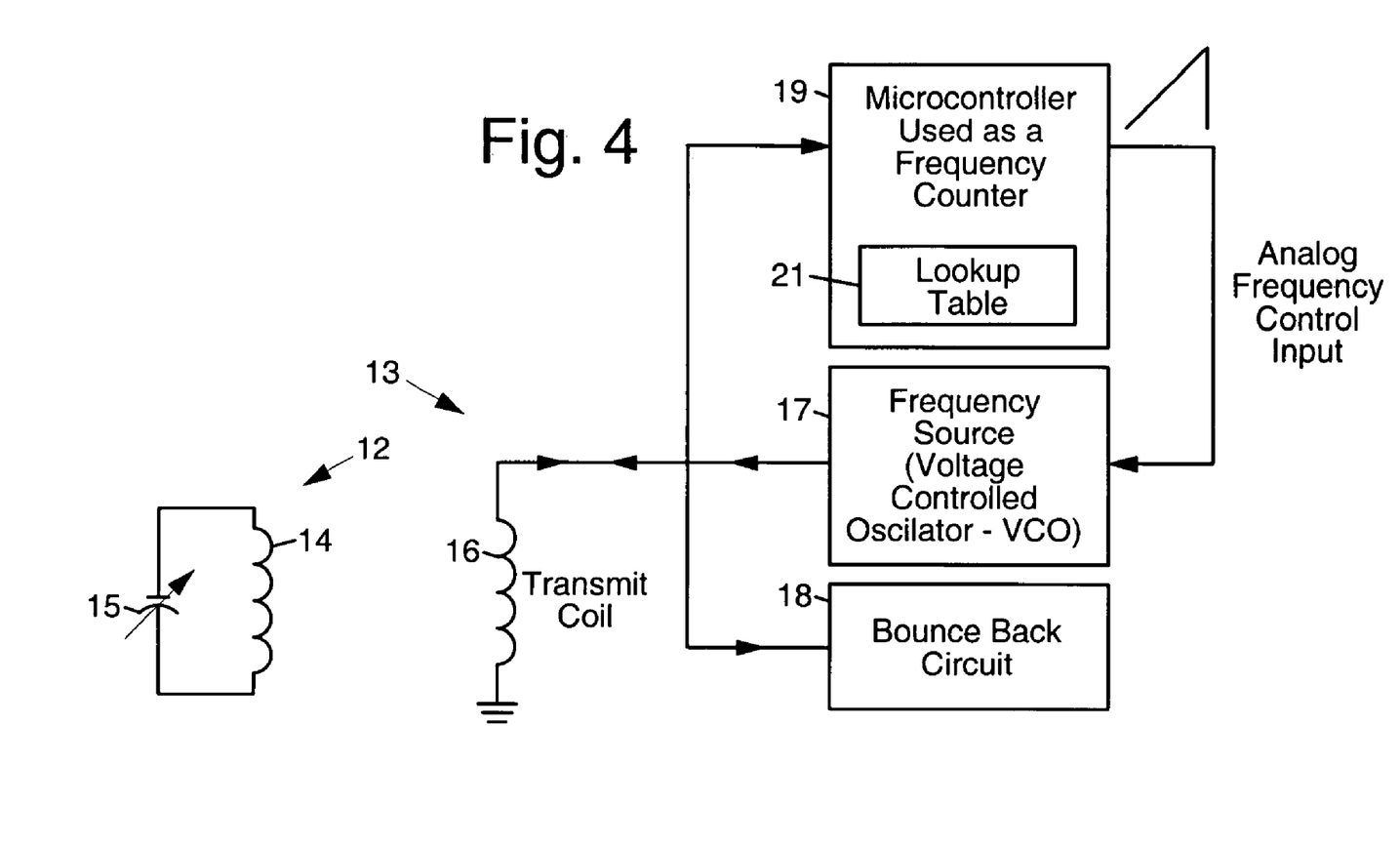

As is shown in FIGS. 2-4, for example, the implantable LC sensor 12 comprises an inductor 14 and a variable capacitor 15. The variable capacitor 15 is the pressure sensitive element of the implanted LC sensor 12.

Exemplary sensors 12 are disclosed in copending applications having Ser. Nos. 11/157,375 and 11/475,905, assigned to the assignee of the present invention, which are incorporated herein by reference in their entirety. Relevant portions of these applications are presented below.

As is disclosed in U.S. patent application Ser. No. 11/157,375, the exemplary sensor 12 is used to measure physical parameters, and in particular blood pressure. The sensor 12 can be fabricated using micro-machining techniques and is small, accurate, precise, durable, robust, biocompatible, and insensitive to changes in body chemistry, or biology. Additionally, the sensor 12 can incorporate radiopaque features to enable fluoroscopic visualization during placement within the body. Furthermore, the sensor 12 is encased in a hermetic, unitary package of electrically insulating material where the package is thinned in one region so as to deform under a physiologically relevant range of pressure. The LC circuit contained in the packaging is configured so that one electrode of the capacitor is formed on the thinned region. The sensor 12 does not require the use of external connections to relay pressure information externally and does not need an internal power supply to perform its function.

The sensor 12 includes a body formed from electrically insulating materials, preferably biocompatible ceramics. In a preferred embodiment, the body is comprised of fused silica. The sensor 12 comprises a deflectable region at a lower end of the body. The body further comprises a lower chamber and an upper chamber.

An LC resonator is hermetically housed within the body and comprises a capacitor and an inductor. As used herein, the term "hermetic" will be understood to mean "completely sealed, especially against the escape or entry of air and bodily fluids." The capacitor is located within the lower cylindrical chamber and comprises at least two plates disposed in parallel, spaced apart relation. The inductor comprises a coil disposed within the upper chamber and which is in conductive electrical contact with the capacitor.

The lower capacitor plate is positioned on the inner surface of the deflectable region of the sensor body. The upper capacitor plate is positioned on a fixed region of the sensor body. A change in ambient pressure at the deflectable region of the sensor 12 causes the deflectable region to bend, thereby displacing the lower plate with respect to the upper plate and changing the capacitance of the LC circuit. Because the change in capacitance of the LC circuit changes its resonant frequency, the resonant frequency of the sensor 12 is pressure-dependent.

Beyond what has been presented in U.S. Pat. Nos. 6,111,520 and 6,278,379 relating to the fundamental operating principle of the wireless pressure sensor 12, additional means to further sensor miniaturization is required in order to achieve an acceptable size for implantation into the heart or the vasculature. The sensor outer dimensions are constrained by the lumen size of the delivery catheter that is used to introduce the sensor. Catheter inner diameters typically range from 1-5 mm. Also, the size and shape of the sensor should minimally interfere with mechanical or hemodynamic function of the heart or vessel where it is located.

Within these physical size constraints, one of the most significant challenges is achieving adequate coupling to the sensor inductor coil from the external readout device at the necessary distance from the outside of the body to the implant site. One method for achieving enhanced coupling is to add magnetic material to the inductor. However, this approach is not feasible in a sensor intended for in vivo use, as the magnetic material would be adverse to magnetic resonance imaging, for example. For a limited coil cross-sectional area, an increased coupling coefficient is also achievable by using a three-dimensional inductor coil configuration, as opposed to two-dimensional designs. For these reasons, a three-dimensional helical inductor coil configuration is the preferred embodiment for the sensor design.

LC Circuit Introduction

The sensor 12 features a completely passive inductive-capacitive (LC) resonant circuit with a pressure varying capacitor. Because the sensor is fabricated using completely passive electrical components and has no active circuitry, it does not require on-board power sources such as batteries, nor does it require leads to connect to external circuitry or power sources. These features create a sensor which is self-contained within the packaging material and lacks physical interconnections traversing the hermetic packaging, such interconnects frequently being cited for failure of hermeticity. Furthermore, other sensing capabilities, such as temperature sensing, can be added using the same manufacturing techniques. For example, temperature sensing capability can be accomplished by the addition of a resistor with known temperature characteristics to the basic LC circuit.

The capacitor in the pressure sensor 12 has at least two conductive elements separated by a gap. If a force is exerted on the sensor, a portion of the sensor 12 deflects, changing the relative position between the at least two conductive elements. This movement will have the effect of reducing the gap between the conductive elements, which will consequently change the capacitance of the LC circuit. An LC circuit is a closed loop system whose resonance is proportional to the inverse square root of the product of the inductor and capacitor. Thus, changes in pressure alter the capacitance and, ultimately, cause a shift in the resonant frequency of the sensor. The pressure of the environment external to the sensor is then determined by referencing the value obtained for the resonant frequency to a previously generated curve relating resonant frequency to pressure.

Because of the presence of the inductor, it is possible to couple to the sensor electromagnetically and to induce a current in the LC circuit via a magnetic loop. This characteristic allows for wireless exchange of electromagnetic energy with the sensor and the ability to operate it without the need for an on-board energy source such as a battery. Thus it is possible to determine the pressure surrounding the sensor by a simple, non-invasive procedure by remotely interrogating the sensor, recording the resonant frequency, and converting this value to a pressure measurement.

One method of sensor interrogation is explained in U.S. patent application Ser. No. 11/105,294, incorporated herein by reference. According to this invention, the interrogating system energizes the sensor 12 with a low duty cycle, gated burst of RF energy having a predetermined frequency or set of frequencies and a predetermined amplitude. The energizing signal is coupled to the sensor via a magnetic loop. The energizing signal induces a current in the sensor 12 that is maximized when the frequency of the energizing signal is substantially the same as the resonant frequency of the sensor. The system receives the ring down response of the sensor 12 via magnetic coupling and determines the resonant frequency of the sensor, which is then used to determine the measured physical parameter. The resonant frequency of the sensor is determined by adjusting the frequency of the energizing signal until the phase of the ring down signal and the phase of a reference signal are equal or at a constant offset. In this manner, the energizing signal frequency is locked to the sensor's resonant frequency and the resonant frequency of the sensor is known. The pressure of the localized environment can then be ascertained.

Q-Factor and Packaging

Q factor (Q) is the ratio of energy stored versus energy dissipated. The reason Q is important is that the ring down rate of the sensor is directly related to the Q. If the Q is too small, the ring down rate occurs over a substantially shorter time interval. This necessitates faster sampling intervals, making sensor detection more difficult. Also, as the Q of the sensor increases, so does the amount of energy returned to external electronics. Thus, it is important to design sensors with values of Q sufficiently high enough to avoid unnecessary increases in complexity in communicating with the sensor via external electronics.

The Q of the sensor is dependent on multiple factors such as the shape, size, diameter, number of turns, spacing between the turns and cross-sectional area of the inductor component. In addition Q will be affected by the materials used to construct the sensors. Specifically, materials with low loss tangents will provide a sensor with higher Q factors.

The body of the implantable sensor 12 is preferably constructed of ceramics such as, but not limited to, fused silica, quartz, pyrex and sintered zirconia, that provide the required biocompatibility, hermeticity and processing capabilities. These materials are considered dielectrics, that is, they are poor conductors of electricity but are efficient supporters of electrostatic or electroquasistatic fields. An important property of dielectric materials is their ability to support such fields while dissipating minimal energy. The lower the dielectric loss, the lower the proportion of energy lost, and the more effective the dielectric material is in maintaining high Q.

With regard to operation within the human body, there is a second important issue related to Q, namely that blood and body fluids are conductive mediums and are thus particularly lossy. As a consequence, when a sensor is immersed in a conductive fluid, energy from the sensor 12 will dissipate, substantially lowering the Q and reducing the sensor-to-electronics distance. It has been found that such loss can be minimized by further separation of the sensor from the conductive liquid. This can be accomplished, for example, by coating the sensor in a suitable low-loss-tangent dielectric material. The potential coating material must also meet stringent biocompatibility requirements and be sufficiently compliant to allow transmission of fluid pressure to the pressure-sensitive deflective region. One preferred material for this application is silicone rubber. It should be appreciated that use of a coating is an optional feature and is not required to practice the invention per se but such coatings will preserve the Q of the sensor which can prove advantageous depending on the intracorporeal location of the sensor, There are various manufacturing techniques that can be employed to realize sensors according to the current invention. Capacitors and inductors made by a variety of methods can be manufactured separately, joined through interconnect methods and encapsulated in hermetic packaging. In one embodiment, the pressure sensitive capacitor and the three-dimensional inductor coil are formed separately and joined together to form the LC circuit. In another embodiment, the capacitor and inductor coil can be manufactured integral with one another. Additionally, there are several methods to create these discrete elements and to join each discrete element to create the final sensor. The following examples are provided to illustrate important design considerations and alternative methods for creating these discrete sensor elements but should not be construed as limiting the invention in any way.

Coil Description:

The inductor coil is comprised of the inductor coil body and the coil leads. Numerous parameters of the inductor coil can be varied to optimize the balance of size and the electrical properties of the circuit, including the materials, coil diameter, wire gage, number of coil windings, and cross-sectional area of the coil body. The material of the coil must be highly conductive and also biocompatible. Suitable materials include, but are not limited to, gold, copper and alloys thereof. If the wire is sufficiently strong, the coil can be self-supporting, also known as an "air core" configuration. A solenoid coil is another suitable configuration. If the wire is not sufficiently strong unsupported to maintain its intended configuration during assembly and in use, the coil can be formed around a central bobbin comprised of a suitable dielectric material. In the alternative, the coil can be encased in a liquid polymer that can cure or otherwise harden after it is applied to the coil body. Polyimide is one preferred material for this application because of its thermal, electrical, and mechanical properties. However, processes achieving substantially similar results that involve lower processing temperatures would make other polymer choices desirable, such choices being obvious to one skilled in the art.

The wire from which the coil is formed can be solid wire, bundled wire or cable, or individually insulated stranded wire.

The wire gage, coil diameter, cross-sectional area of the coil body, and number of windings all influence the value of inductance and the detection range of the circuit. As any of these properties increase, so do the size and the inductance of the coil, as well as the sensor-to-electronics distance. To specify an inductor coil for use in the sensor, size considerations must be balanced with those of inductance and Q.

A small scale three-dimensional inductor coil can be formed in a variety of ways. It can be created conventionally. One such method is machine coil winding of small diameter insulated magnet wire.

In another embodiment, a three-dimensional inductor coil is built onto the top of one of the through connections terminals on the backside of the capacitor plate substrate, using integrated circuit processing techniques and a multitude of layers. This coil can be defined and supported by photo-definable dielectric material such as photo-definable polyimide. In the disclosed embodiment, the coil is free standing in air, supported by same-material mechanical elements that are strategically positioned to minimize the effect of the supporting mechanical elements on the electrical function of the coil.

In this approach it is desirable to minimize the number of design layers to improve batch process yield and to reduce processing time. In a conventional configuration, a spacing layer is required between each winding, making the number of layers required equal to two times the number of windings. In one version of the three-dimensional coil design, each subsequent coil is alternately spaced slightly smaller or larger in diameter than the previous winding. This configuration creates a small separation between adjacent coils in the x-y plane, eliminating the need for an extra vertical spacing layer in between windings. This configuration results in a number of coil windings equal to the number of layers, which is more practical for manufacturing using a MEMS approach.

In yet another embodiment, a three-dimensional inductor coil is built onto the surface of a cylinder of an appropriate material such as, but not limited to fused silica. A conductive layer is first applied to the surface of the cylinder. Then a mold is formed onto the surface so that parts of the underlying conductive surface are exposed and some are covered. A metal may then be formed onto the exposed areas by electroplating, sputtering or vapor deposition. The exposed area forms a helical trench that extends along the surface of the cylinder, thus realizing an inductor coil.

Capacitor Description

The pressure sensitive capacitor plates are formed on two separate substrate wafers in recessed trenches. At least one of the wafers has a substrate thickness in the region of the capacitive plate such that sufficient plate deflection occurs due to external pressure change, resulting in a sufficient change in resonant frequency per unit pressure (mm Hg) once the LC circuit has been created. If necessary, the thickness of the wafer 40 in the region can be reduced by suitable chemical or mechanical means, as indicated by the dashed line, to provide the desired range of deflection.

The wafers are bonded together such that the capacitive plates are parallel and separated by a gap on the order of 0.1-10 microns, preferably 0.1-2 microns.

The performances of the sensor, especially the propensity of its capacitance and, in turn, its resonant frequency to change as a response to an environmental pressure change, are closely related to few fundamental geometrical considerations. Widening or elongating the deflective region will augment its mechanical flexibility, and, in turn, the pressure sensitivity of the sensor. Decreasing the thickness of the deflective area will result in similar improvements. However, thinner deflective region can become too fragile or otherwise more sensitive to systemic response from the host-organism other than changes in mean and pulsatile blood pressure (ex: hyperplasia, tissue overgrowth, etc.). Reducing the gap, while maintaining adequate deflective region thickness, offers a complementary alternative to insufficiently low sensitivity. As the initial value of the gap is shrinking, the motion of the deflective region relative to the initial gap becomes proportionally more important. This results in a greater change in capacitance for a given stimulus, therefore enhancing the pressure sensitivity. While relevant sensitivity can be achieved with initial air-gap ranging from 0.1 to 10 micrometers, initial air-gaps ranging from a 0.1 to 2 micrometers are preferable.

To insure adequate pressure range, the value of the maximum deflection under maximum load (indexed, for exampled, on physiologically relevant maximum pulsatile blood pressure values, at relevant location in the host-organism) ought to be, in theory, inferior or equal to the value of the initial gap. In practice, limiting the maximum deflection under maximum load to represent only a fraction of the initial gap (ex: 0.6 micrometer for a 1 micrometer initial gap) will ease the fabrication constraints and result in a more robust an versatile sensor.

One suitable method for creating the pressure sensitive capacitor is by electroplating the individual plates in the recessed trenches on a substrate wafer to a given height H1, H2 that is less than or equal to the depth D1, D2 of the respective trench. When the wafers are bonded together the capacitive plates are generally separated by the difference between the sum of the trench depths and the sum of the plate heights, (D1+D2)−(H1+H2). An inherent variation in the height of the plates and the required range of deflection for the full operating pressure range are parameters which determine the initial separation distance (a.k.a., the gap).

Assembled wafers and capacitor plates may be laser-cut around their peripheries, reducing the capacitor to its final size and hermetically fusing the two wafers together. A CO2 laser can be used at a peak wavelength of about 10 microns if the substrate is fused silica. Power must be sufficiently large to cut and fuse the wafers together, while at the same time being sufficiently small that the internal components of the sensor are not damaged by excessive heat.

In an alternative method, the wafers are pre-bonded using glass frit to produce a hermetic seal around the cavities. In this method, the laser cut only releases the sensors from the wafer, and does not provide the primary means of creating the hermetic seal. Other suitable methods of hermetically sealing the wafers include, but are not limited to, adhesives, gold compression bonding, direct laser bonding, and anodic bonding.

In another alternative embodiment, one plate may be formed on a substrate wafer having a trench with a depth greater that of the trench in the substrate wafer. The other plate is formed on the inner surface of a wafer without a trench. When imposed in face-to-face relation, the plate is received into the lower end of the trench with the plates disposed in parallel, spaced-apart relation.

To achieve smaller gap separation distances on the order of 0.1-2 microns, revised processing methods are employed to bring additional control to the variation in height across the conductive plates. One method is as follows: the conductive plate is built to a target height that slightly exceeds the depth of the recess trench. In this embodiment the plates may be formed by electroplating. Preferred materials for the plates are copper, gold, and alloys thereof. After building the plates, each conductive plate is polished using chemical/mechanical polishing (CMP) to planarize and reduce the height of the plate until it is less than the depth of the trench by the desired amount.

Another method also begins with the plates formed to a height that slightly exceeds the depth of the trenches. The metal capacitor plates are mechanically polished to planarize the metal surface down to the surface of the substrate. Following this step, the metal plates are chemically etched by a selective etchant to a height that achieves a desired difference in height between the height of the plate and the depth of the trench.

Still another method for forming the plates is physical vapor deposition (PVD), also known as thin film deposition, in conjunction with photolithography. PVD is used to deposit a uniform layer of metal, sub-micrometer to tens of micrometers thick, on a wafer. Subsequently a layer of photoresist is deposited, a mask is used to pattern the photoresist, and a selective etching technique is utilized to etch away the extra metal and to define the desired pattern. Other methods of defining the metal pattern can be utilized, such as, shadow-masking, a method well known in the art.

In one approach, a pressure sensitive capacitor can be formed by separating the bottom conductive pad into two separate regions that capacitively couple to one another via a common third conductive region on the pressure sensitive deflective region. The inductor coil is then electrically connected, one lead of the coil to the first region, and the other lead of the coil to the second region.

When the split-plate design is employed for one side of the capacitor, the split plates are preferably located on the fixed side of the capacitor (i.e., opposite the pressure-sensitive side), because the electrical/mechanical interconnects made to the split plates in order to complete the LC circuit are less prone to mechanical failure when the surface to which they are mechanically attached does not deflect or move repetitively.

In yet another embodiment, the plate on the top wafer is separated by a dielectric into two conductive regions, with one region substantially larger than the other. After bonding together of the two wafers, the smaller conductive region is electrically connected to the outer edge of the pressure sensitive plate, spanning the air gap with a laser weld that is performed through the substrate material. The laser wavelength is selected so that it is passes through the substrate material with minimal energy absorption, but heats the conductive plate sufficiently to produce the weld connection between the top and bottom plates.

Interconnects and Methods

It will be appreciated that sensors 12 can have capacitive and inductive elements maintained in separate hermetic cavities or that these elements may be contained in a single hermetic cavity.

In one embodiment, the pressure sensitive capacitor needs to be connected to the three-dimensional inductor coil while maintaining a hermetic seal around the internal cavity that defines the separation gap between the capacitive plates. This can be achieved by using a variety of through-wafer interconnection methods, familiar to those skilled in the art. Through holes or vias are formed in an upper wafer to provide mechanical and electrical access to a pair of upper capacitor plates. The wafer through-holes can be formed before or after plate formation using some combination of the following techniques: laser drilling, chemical (wet) etching, conventional or ultrasonic machining, or dry etching. The vias can optionally be filled with gold, copper, or other suitable conductive material to form through-wafer interconnects in conductive communication with the capacitor plates. The through-wafer interconnects thus form a hermetic seal. Leads from an inductor coil are attached to the through-wafer interconnects to place the leads in conductive communication with the capacitor plates.

The through holes or vias are formed in an upper wafer to provide mechanical and electrical access to a pair of lower capacitor plates. Electrical connections to the lower capacitor plates will be accomplished through leads of the inductor coil (not shown) or through wires or other suitable conductive means.

Thermosonic or ultrasonic bonding can be used to connect the inductor coil to either an electrode of a capacitor or a through-wafer interconnect. Thermosonic and ultrasonic bonding are types of wire bonding used for metal wires including, but not limited to, gold wires. Typical temperatures required for thermosonic bonding are between 125-220° C., and bonding occurs when a combination of static and ultrasonic mechanical and thermal energy is delivered to the metallic coil wire to be bonded to a metal surface. Ultrasonic bonding is performed just as thermosonic bonding but without the use of heat. Useful materials for the metallized bond sites and coil comprise gold, copper and aluminum and alloys thereof. Bonds can be formed between certain dissimilar metals as well as between all like metals, and such combinations are widely known in the art.

If the metal or metal alloy used for the coil has a dielectric (e.g., polymer) coating, the coating must be removed prior to bonding. The coating can be removed to expose the metal at the adhesion point so that bonding can occur by either mechanical or chemical means. Alternatively, the parameters (e.g. time, heat, pressure) of the thermosonic bonding process can be altered and the geometry of the bonding tool modified so that reliable mechanical and electrical interconnects are created. Such modifications cause the coating material to be pushed aside, exposing the metal at the bonding site and extruding the wire slightly. This latter technique provides certain advantages because it reduces the number of manufacturing steps.

An alternative method of conductively connecting the coil to the capacitive plates is a solder bump. Solder is applied to the metal-metal interface of the coil and electrode or interconnect to form a mechanical and electrical connection. This method can be used for capacitor plate or through-wafer interconnections. Lead-free solder should be used for biocompatibility. Connection can also be achieved through IC processing techniques, which allow for plates and coils to be formed in electrical contact with one another. Finally laser welds, as previously discussed, can be used to achieve electrical/mechanical interconnects.

As is disclosed in U.S. patent application Ser. No. 11/475,905, the sensor 12 may preferably have an outer coating of biocompatible silicone. The sensor 12 may comprise a wire spiral inductor coil positioned in planar fashion in a substrate. Optionally, the sensor 12 may have recesses, each with a hole, to receive a tether wire for delivery of the device into a human patient, as described below. The sensor 12 comprises a wire that connects the coil to a capacitor plate positioned within the coil.

The sensor 12 comprises a lower substrate and an upper substrate. The lower substrate and upper substrate are constructed from a suitable material, such as glass, fused silica, sapphire, quartz, or silicon. Fused silica is the preferred material of construction. The lower substrate has on its upper surface an induction coil, and upper substrate has a recess with a surface having an induction coil thereon. The top surface of upper substrate forms a membrane capable of mechanically responding to changes in a patient's physical property, such as pressure. The end of sensor 12 has a notch or recess. A wire connects the lower capacitor plate to induction coil.

The size of the sensors 12 will vary according to factors such as the intended application, the delivery system, etc. Oval sensors 12 are intended to be from about 0.5 in. to about 1 in. in length and from about 0.1 in. to about 0.5 in. in width, with a thickness of from about 0.05 in. to about 0.30 in.

The upper substrate can be significantly thinner than the lower substrate. By way of example, the upper substrate may be from about 100 to about 300 microns thick, whereas the lower substrate may be from about 500 to about 1500 microns thick. In an alternative embodiment, both substrates may be of the same thickness ranging from about 100 to about 1000 microns.

The sensor 12 may be attached to a hollow tube that has a flexible tip. The tethering system may include proximal holes and distal holes disposed in the hollow tube. A tether wire may be attached to sensor 12 at sensor holes and hollow tube holes, and a tether wire may be positioned slidably within the hollow tube.

The pressure sensor 12 can be manufactured using micromachining techniques that were developed for the integrated circuit industry. An example of this type of sensor 12 features an inductive-capacitive (LC) resonant circuit with a variable capacitor, as is described in Allen et al., U.S. Pat. Nos. 6,111,520 and 6,278,379, which are incorporated herein by reference. The sensor 12 contains two types of passive electrical components, namely, an inductor and a capacitor. The sensor 12 is constructed so that the fluid pressure at the sensor's surface changes the distance between the capacitor's substantially parallel plates and causes a variation of the sensor's capacitance.

In a preferred embodiment the sensor 12 is constructed using a series of steps that use standard MEMS manufacturing techniques.

In a first step of this process, a thin layer of metal (Protective mask) is deposited onto the top and bottom surface of a fused silica wafer (alternative materials are glass, quartz, silicon or ceramic). Wafer diameters can range from about 3 to about 6 in. Wafer thickness can range from about 100 to about 1500 microns. A pattern mask is then created on one side of the wafer to define the location of cavities that need to be etched into the surface.

Trenches or cavities are etched into one surface of the wafer to depths ranging from about 20 to about 200 microns. This etching is accomplished using any combination of standard wet and dry etching techniques (acid etch, plasma etch, reactive ion etching) that are well known in the MEMS industry. The protective metal mask is removed using standard metal etching techniques.

A thin metal seed layer (typically chromium) is deposited on the etched side of the wafer using standard metal deposition techniques such as sputtering, plating or metal evaporation. A layer of photo-resistive material is applied to the etched surface of the wafer using standard spin coating procedures.

A mask aligner and UV light is used in a photolithographic processes to transfer a pattern from a mask to the photoresist coating on the wafer. The non-masked portions of the Photoresist are removed chemically creating a mold 106 of the desired coil pattern. Copper is electroplated into the mold to the desired height, typically from about 5 to about 35 microns. In FIG. 23, the Photoresist 110 and seed layer 112 are etched away leaving the plated copper coils 114. This process is then repeated with a second wafer. The two processed wafers are aligned such that the cavities with plated coils are precisely orientated in over one another and temporarily bonded to each other.

By using a $CO_2$ laser (or other appropriate laser type), the individual sensors are cut from the glass wafer. The laser cutting process results in a permanent, hermetic seal between the two glass wafers. The laser energy is confined to a precise heat effect zone in which the hermetic seal is created.

An embodiment of the sensor may be attached to a delivery catheter and has a stabilizer or basket. The stabilizer can be any appropriate device or structure that can be fixedly attached to a sensor of the invention to assist the sensor in maintaining position, location, and/or orientation after the sensor is delivered to an intended site. The stabilizer can comprise any appropriate physiologically acceptable rigid or slightly flexible material, such as stainless steel, nitinol, or a radiopaque metal or alloy.

The design of the sensor 12 provides many important benefits to sensor performance. The hermetic seal created during the laser cutting process, coupled with the design feature that the conductor lines of the sensor are sealed within the hermetic cavity, allows the sensor to remain stable and drift free during long time exposures to body fluids. In the past, this has been a significant issue to the development of sensors designed for use in the human body. The manufacturing methodology described above allows many variations of sensor geometry and electrical properties. By varying the width of the coils, the number of turns and the gap between the upper and lower coils the resonant frequency that the device operates at and the pressure sensitivity (i.e., the change in frequency as a result of membrane deflection) can be optimized for different applications. In general, the design allows for a very small gap between the coils (typically between about 3 and about 35 microns) that in turn provides a high degree of sensitivity while requiring only a minute movement of the coils to sense pressure changes. This is important for long term durability, where large membrane deflection could result in mechanical fatigue of the pressure sensing element.

The thickness of the sensor 12 may also be varied to alter mechanical properties. Thicker wafers are more durable for manufacturing. Thinner sensors 12 allow for creating of thin pressure sensitive membranes for added sensitivity. In order to optimize both properties the sensors may be manufactured using wafers of different thicknesses. For example, one side of the sensor may be constructed from a sensor of approximate thickness of about 200 microns. This wafer is manufactured using the steps outlined above. Following etching, the thickness of the pressure sensitive membrane (i.e., the bottom of the etched trench) is in the range of from about 85 to about 120 microns. The matching wafer is from about 500 to about 1000 microns thick. In this wafer, the trench etching step is eliminated and the coils are plated directly onto the flat surface of the wafer extending above the wafer surface a height of from about 20 to about 40 microns. When aligned and bonded, the appropriate gap between the top and bottom coils is created to allow operation preferably in a frequency range of from 30 to 45 MHz and have sensitivity preferably in the range of from 5 to 15 kHz per millimeter of mercury. Due to the presence of the about 500 to about 1000 micron thick wafer, the sensor 12 has added durability for endovascular delivery and for use within the human body.

The sensor 12 exhibits the electrical characteristics associated with a standard LC circuit. An LC circuit can be described as a closed loop with two major elements, a capacitor and an inductor. If a current is induced in the LC loop, the energy in the circuit is shared back and forth between the inductor and capacitor. The result is an energy oscillation that will vary at a specific frequency. This is termed the resonant frequency of the circuit and it can be easily calculated as its value is dependent on the circuit's inductance and capacitance. Therefore, a change in capacitance will cause the frequency to shift higher or lower depending upon the change in the value of capacitance.

As noted above, the capacitor in the assembled pressure sensor includes two circular conductive segments separated by an air gap. If a pressure force is exerted on these segments it will act to move the two conductive segments closer together. This will have the effect of reducing the air gap between them which will consequently change the capacitance of the circuit. The result will be a shift in the circuit's resonant frequency that will be in direct proportion to the force applied to the sensor's surface.

Because of the presence of the inductor, it is possible to electromagnetically couple to the sensor and induce a current in the circuit. This allows for wireless communication with the sensor and the ability to operate it without the need for an internal source of energy such as a battery. The readout device generates electromagnetic energy that penetrates through the body's tissues to the sensor's implanted location. The sensor's electrical components absorb a fraction of the electromagnetic energy that is generated by the readout device via inductive coupling. This coupling induces a current in the sensor's circuit that oscillates at the same frequency as the applied electromagnetic energy. Due to the nature of the sensor's electro-mechanical system there exists a frequency of alternating current at which the absorption of energy from the readout device is at a maximum. This frequency is a function of the capacitance of the device. Therefore, if the sensor's capacitance changes, so will the optimal frequency at which it absorbs energy from the readout device. Since the sensor's capacitance is mechanically linked to the fluid pressure at the sensor's surface, a measurement of this frequency by the readout device gives a relative measurement of the fluid pressure. If calibration of the device is performed, then an absolute measurement of pressure can be made. See, for example, the extensive discussion in the Allen et al. patent, again incorporated herein by reference, as well as Gershenfeld et al., U.S. Pat. No. 6,025,725, incorporated herein by reference. Alternative readout schemes, such as phase-correlation approaches to detect the resonant frequency of the sensor, may also be employed.

The pressure sensor 12 is made of completely passive components having no active circuitry or power sources such as batteries. The pressure sensor 12 is completely self-contained having no leads to connect to an external circuit or power source. Furthermore, these same manufacturing techniques can be used to add additional sensing capabilities, such as the ability to measure temperature by the addition of a resistor to the basic LC circuit or by utilizing changes in the back pressure of gas intentionally sealed within the hermetic pressure reference to change the diaphragm position and therefore the capacitance of the LC circuit.

The frequency response to the sensor 12 is in the range of from about 1 to about 200 MHz, preferably from about 1 to about 100 MHz, and more preferably from about 2 to about 90 MHz, and even more preferably from about 30 to about 45 MHz, with a Q factor of from about 5 to about 150, optimally from about 5 to about 80, preferably from about 40 to about 100, more preferably from about 50 to about 90.

In another embodiment of the sensor 12, there is no direct conductor-based electrical connection between the two sides of the LC circuit. Referring to the sensor described in the Allen et al. patents, the device is constructed using multiple layers upon lie the necessary circuit elements. Disposed on the top and bottom layer are metal patterns constructed using micro-machining techniques which define a top and bottom conductor and a spiral inductor coil. To provide for an electrical contact between the top and bottom layers small vias or holes are cut through the middle layers. When the layers are assembled, a metal paste is forced into the small vias to create direct electrical connections or conduits. However, experimentation has shown that due to additional capacitance that is created between the top and bottom inductor coils, a vialess operational LC circuit can be created. This absence of via holes represents a significant improvement to the sensor in that it simplifies the manufacturing process and, more importantly, significantly increases the durability of the sensor making it more appropriate for use inside the human body.

A significant design factor that relates to the performance of the sensor 12 and the operation of the system is the Quality factor (Q) associated with the sensor. The value of Q is one of the key determinates as to how far from the sensor the external readout electronics can be located while still maintaining effective communication. Q is defined as a measure of the energy stored by the circuit divided by the energy dissipated by the circuit. Thus, the lower the loss of energy, the higher the Q. Additional increases in Q can be achieved by removing the central capacitive plate and using capacitive coupling between the copper coils to act as the capacitor element.

In operation, energy transmitted from the external read-out electronics is stored in the LC circuit of the sensor 12. This stored energy induces a current in the LC loop which will cause the energy to be shared back and forth between the inductor and capacitor. The result is an oscillation that will vary at the resonant frequency of the LC circuit. A portion of this oscillating energy is then coupled back to the receiving antenna of the read-out electronics. In high Q sensors, most of the stored energy is available for transmission back to the electronics, which allows the distance between the sensor 12 and the receiving antenna to be increased. Since the transmitted energy will decay exponentially as it travels away from the sensor 12, the lower the energy available to be transmitted, the faster it will decay below a signal strength that can be detected by the receiving antenna and the closer the sensor 12 needs to be situated relative to the receiving electronics. In general then, the lower the Q, the greater the energy loss and the shorter the distance between sensor and receiving antenna required for sensor detection.

The Q of the sensor 12 will be dependent on multiple factors such as the shape, size, diameter, number of turns, spacing between turns and cross-sectional area of the inductor component. In addition, Q will be greatly affected by the materials used to construct the sensor 12. Specifically, materials with low loss tangents will provide the sensor 12 with higher Q factors.

The implantable sensor 12 is preferably constructed of various glasses or ceramics including but not limited to fused silica, quartz, pyrex and sintered zirconia, that provide the required biocompatibility, hermeticity and processing capabilities. Preferably the materials result in a high Q factor. These materials are considered dielectrics, that is, they are poor conductors of electricity, but are efficient supporters of electrostatic or electroquasiatatic fields. An important property of dielectric materials is their ability to support such fields while dissipating minimal energy. The lower the dielectric loss (the proportion of energy lost), the more effective the dielectric material in maintaining high Q. For a lossy dielectric material, the loss is described by the property termed "loss tangent." A large loss tangent reflects a high degree of dielectric loss.

With regard to operation within the human body, there is an important issue related to Q, namely, that blood and body fluids are conductive mediums and are thus particularly lossy. The consequence of this fact is that when a sensor 12 is immersed in a conductive fluid, energy from the sensor 12 will dissipate, substantially lowering the Q and reducing the sensor-to-electronics distance. For example, the sensors 12 described above were immersed in saline (0.9% salt solution), and the measured Q decreased to approximately 10. It has been found that such loss can be minimized by further separation of the sensor from the conductive liquid. This can be accomplished, for example, by encapsulating the sensor 12 in a suitable low-loss-tangent dielectric material. However, potential encapsulation material must have the flexibility and biocompatibility characteristics of the sensor material and also be sufficiently compliant to allow transmission of fluid pressure to the pressure sensitive diaphragm. A preferred material for this application is polydimethylsiloxane (silicone).

As an example, a thin (i.e., 200 micron) coating of silicone was applied to the sensor 12. This coating provided sufficient insulation to maintain the Q at 50 in a conductive medium. Equally important, despite the presence of the silicone, adequate sensitivity to pressure changes was maintained and the sensor retained sufficient flexibility to be folded for endovascular delivery. One additional benefit of the silicone encapsulation material is that it can be optionally loaded with a low percentage (i.e., 10-20%) of radio-opaque material (e.g., barium sulfate) to provide visibility when examined using fluoroscopic x-ray equipment. This added barium sulfate will not affect the mechanical and electrical properties of the silicone.

As described above, it is desirable to increase the Q factor of a sensor 12, and the Q factor can be increased by suitable selection of sensor materials or a coating, or both. Preferably both are used, because the resulting high Q factor of a sensor prepared in this fashion is especially suitable for the applications described.

As disclosed in the Allen et al. patents, several different excitation systems can be used. The readout device generates electromagnetic energy that can penetrate through the body's tissues to the sensor's implanted location. The sensor's electrical components can absorb a fraction of the electromagnetic energy that is generated by the readout device via inductive coupling. This coupling will induce a current in the sensor 12 that will oscillate at the same frequency as the applied electromagnetic energy. Due to the nature of the sensor's electromechanical system there will exist a frequency of alternating current at which the absorption of energy from the readout device is at a minimum. This frequency is a function of the capacitance of the device. Therefore, if the sensor's capacitance changes so will the frequency at which it minimally absorbs energy from the readout device. Since the sensor's capacitance is mechanically linked to the fluid pressure at the sensor's surface, a measurement of this frequency by the readout device can give a relative measurement of the fluid pressure. If calibration of the device is performed then an absolute measurement of pressure can be made.

The circuitry used to measure and display pressure may be contained within a simple to operate, portable electronic unit. This unit also contains the antenna needed to perform the electromagnetic coupling to the sensor 12. The antenna may be integrated into a housing for the electronics or it may be detachable from the unit so that it can be positioned on the surface of the body in proximity to the implanted sensor and easily moved to optimize the coupling between antenna and sensor 12. The antenna itself may consist of a simple standard coil configuration or my incorporate ferrous elements to maximize the coupling efficiency. The electronic device would feature an LCD or LED display designed to clearly display the recorded pressure in physiologically relevant units such as mm Hg. In an alternative embodiment, the display may be created by integrating a commercially available hand-held computing device such as a Palm® or microPC into the electronic circuitry and using this device's display unit as the visual interface between the equipment and its operator. A further advantage of this approach is that the hand-held computer could be detached from the read-out unit and linked to a standard desktop computer. The information from the device may thus be downloaded into any of several commercially available data acquisition software programs for more detailed analysis or for electronic transfer via hard media or the interne to a remote location.

Referring again to FIG. 2, for example, the external electronics unit 13 comprises a transmit coil 16 which is coupled to a frequency source 17 and a bounce back circuit 18. The transmit coil 16 of the external electronic unit 13 is energized by the frequency source 17. The frequency source 17 is varied, and when the frequency corresponds to the resonant frequency of the LC sensor 12, energy bounces back from the transmit coil 16 to the bounce back circuit 18 and is detected and processed to output the corresponding blood pressure of the patient.

As is shown in FIG. 3, an exemplary frequency source 17 may be implemented using direct digital synthesis (as opposed to an analog voltage controlled oscillator, VCO, for example). Although expensive and relatively large, the direct digital synthesizer may be programmed to an exact frequency by a microcontroller (or direct digital synthesis integrated circuit) via digital control lines (frequency control inputs) as shown in FIG. 3.

To implement the electronic unit 13, the circuitry shown in FIG. 4, for example, may be employed. FIG. 4 illustrates a frequency source 17 implemented using a voltage controlled oscillator 17 which is controlled by a microcontroller 19 that is also used as a frequency counter. An analog sweep voltage from the digital-to-analog (D/A) output of a microcontroller 19 drives the analog frequency control input of the frequency source 17 (voltage controlled oscillator 19). The frequency source 17 energizes the transmit coil 16 with pulses of differing frequency. When the frequency of the signals applied to the transmit coil 16 corresponds to the resonant frequency of the LC sensor 12, energy bounces back to the transmit coil 16 that is connected to the bounce back processing circuit 18. This energy is processed to produce a blood pressure reading.

On unique aspect of the electronics unit 13 shown in FIG. 4, for example, relates to frequency generation and calibration. The frequency generation element is not a direct digital synthesizer (DDS), but is a voltage controlled oscillator (VCO) 17. The frequency of the VCO 17 is controlled by an analog voltage, but only a rough idea of the VCO output frequency is known, even if the exact value of the analog input voltage is known.

One innovative aspect of the embodiment of the hypertension system 10 shown in FIG. 4 is that the output frequency of the VCO 17 is routed back into an input capture port of the microcontroller 19, so that microcontroller 19 can measure the exact VCO output frequency. In a wireless blood pressure monitoring application, the analog input voltage to the VCO 17 is swept over its entire range during initial calibration, and the output frequency is measured at discrete steps as the analog input voltage is stepped through its range. This can be done during power up calibration, or in real time.

During power up calibration a lookup table 21 of sixteen (16) points, for example, is created in a memory of the microcontroller 19 that correlates sixteen (16) analog input voltage to sixteen (16) frequencies. At voltage levels between the values in the lookup table 21, the output frequency may be determined by interpolating values in the lookup table. The frequency sweep range of the VCO 17 may be 200-400 MHz, for example, and for an analog input range of 0 to 9 volts, the use of a VCO 17 with this type of calibration is a considerable savings in power. cost, and size compared to using a direct digital synthesis (DDS) implementation.

Figure 5:
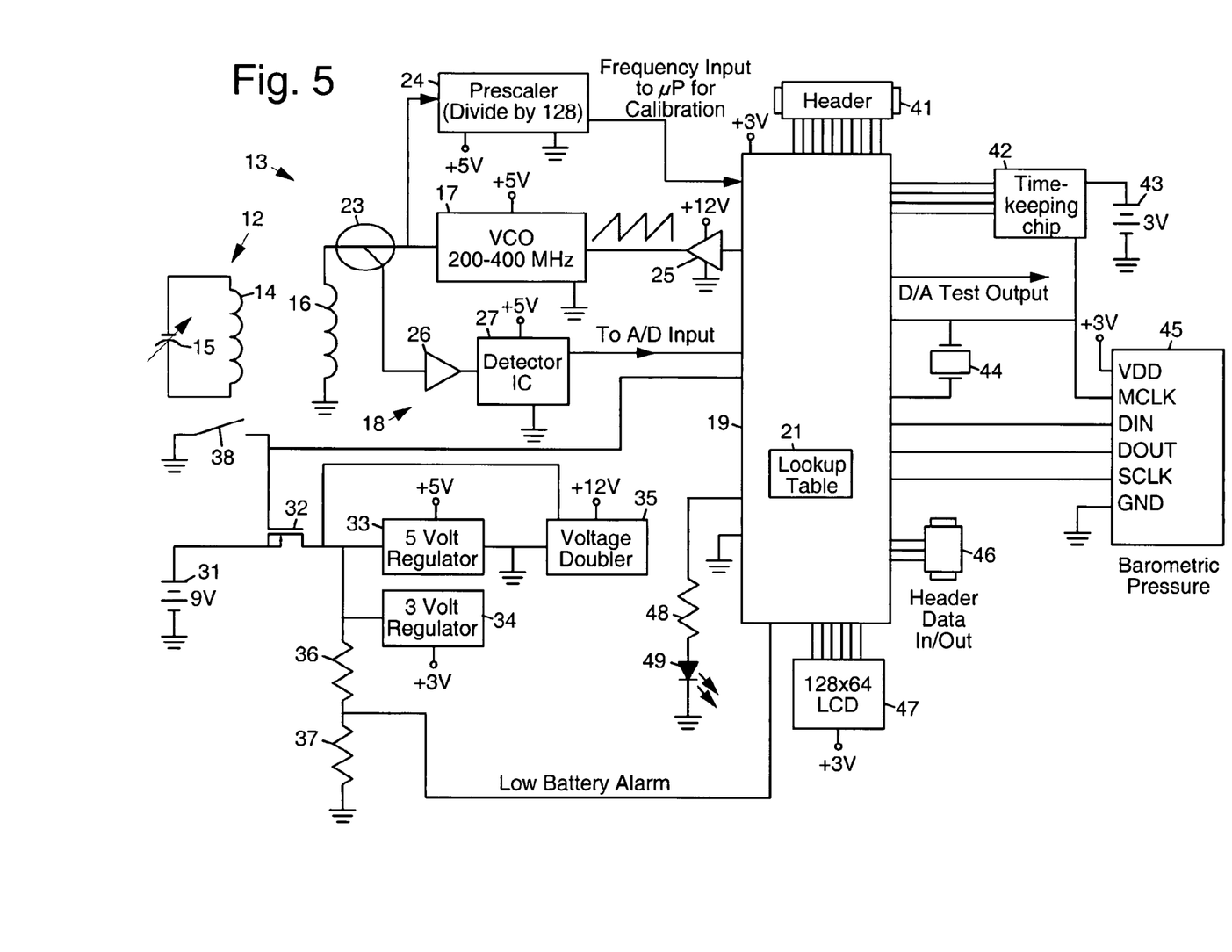
FIG. 5 is a detailed block diagram of the hypertension system shown in FIG. 4.

FIG. 5 is one possible detailed block diagram of the hypertension system 10 shown in FIG. 4. As is shown in FIG. 5, the hypertension system 10 comprises the implantable LC sensor 12, which includes the inductor 14 and variable capacitor 15. The transmit coil 16 is coupled to a 10 dB directional coupler 23, for example. A first output of the directional coupler 23 is coupled to the voltage controlled oscillator (VCO) 17 and to a divide by 128 prescaler 24, for example. An output of the prescaler 24 is coupled to the input capture pin of a microcontroller (µP) 19 to determine the frequency at any given time. The microcontroller19 may be an Analog Devices model ADUC7020 microcontroller 19, for example. A digital-to-analog (D/A) output of the microcontroller 19 is coupled by way of a rail-to-rail operational amplifier 25 to an analog input of the VCO 17.

A second output of the directional coupler 23 is coupled to the bounce back circuit 18. The bounce back circuit 18 comprises an amplifier 26, which may have a 14 dB gain, which is coupled to a detector 27, such as an Analog Devices model AD8361 RF detector integrated circuit, for example. The output of the detector 27 is coupled to an analog input of the microcontroller 19. In this manner, the frequency at which the maximum energy is absorbed by the LC sensor 12 is determined in a fashion similar to a one port network analyzer.

Power for the microcontroller 19 may be provided by a 9 volt power source 31, such as a nine volt battery, for example coupled to a MOSFET 32. The MOSFET 32 acts as a power controller and is also coupled to various voltage regulators 33, 34, including a twelve volt power source and a voltage doubler 35, such as a model ICL7660 voltage doubler, for example. Inputs to the five volt and three volt regulators 33, 34, and the voltage doubler 35 are coupled by way of a resistive voltage divider comprising two series resistors 36, 37 to ground. A low battery alarm signal is coupled from a point between the two series resistors 36, 37 to the microcontroller 19. A push-button toggle switch 38 is used to ground the input of the MOSFET 32 to turn the unit off, or on. Various other power controller integrated circuits may also be used as on-off controllers.

The microcontroller 19 is coupled to a first header 41 which is used to various general purpose functions, as required by design or testing. A three volt power source 43, such as a three volt battery, for example, is coupled to a timekeeping chip 42, such as a DS1302 time and date chip. In this fashion, the blood pressure reading can be time and date stamped. In this embodiment, the master clock drives the timekeeping chip 42, and the barometric pressure integrated circuit 45, such as an MS5534 barometric module, and the microcontroller 19, for example. The barometric pressure integrated circuit 45 is also coupled to the microcontroller 19 by a standard three wire interface, and receives a digital input signal (DIN) and clock signal (SCLK) therefrom, and outputs a digital pressure signal (DOUT) thereto. The purpose of the barometric pressure circuit is to compensate the blood pressure reading depending on the atmospheric pressure at the time of the reading.

A crystal oscillator 44, such as a 32.768 KHz oscillator, for example, is coupled to the microcontroller 19, the timekeeping chip 42, and to the barometric pressure integrated circuit 45. The microcontroller 19 is also coupled to a data input/output header 46 which is used to communicate between the microcontroller 19 and external circuitry, such as a dial up modem, handheld computer, or any serial device that is designed to accept data from the electronic unit 13, for example. The microcontroller 19 is also coupled to a liquid crystal display (LCD) 47, such as a model AGM1264K LCD, for example. The LCD 47 is used to display the blood pressure of the patient, or various other indications such as systolic and diastolic pressure, as required.

The microcontroller 19 is also coupled by way of a resistor 48 to a light emitting diode (LED) 49. The light emitting diode 49 is used in this implementation to indicate that the system has locked to the resonant frequency of the implanted sensor 12 and is working properly. This function is especially important to the user, if a particular implementation of the electronic unit 13 does not use some type of display.

An exemplary hypertension monitoring methods are as follows. The exemplary hypertension monitoring method comprises implanting a blood pressure sensor beneath skin of a wrist of a patient, and wirelessly monitoring and recording blood pressure of the patient. Implanting the blood pressure sensor may comprise configuring an inductive-capacitive (LC) sensor to resonate at a frequency corresponding to the blood pressure of the patient, wherein the resonant frequency output by the inductive-capacitive (LC) sensor corresponds to the blood pressure of the patient. Wirelessly monitoring the blood pressure of the patient may comprise transmitting a variable frequency signal by way of a transmit coil, detecting a resonant frequency signal corresponding to the resonant frequency of the blood pressure sensor in the patient using a bounce back circuit coupled to the transmit coil, and processing the resonant frequency signal bounced back from the bounce back circuit to determine the blood pressure of the patient.

Thus, wireless blood pressure monitoring systems and methods have been disclosed. It is to be understood that the above-described embodiments are merely illustrative of some of the many specific embodiments that represent applications of the principles discussed above. Clearly, numerous and other arrangements can be readily devised by those skilled in the art without departing from the scope of the invention.

What is claimed is:

1. A system comprising:
   an implantable sensor assembly configured to resonate at a frequency corresponding to a physiological blood pressure of a patient, the sensor assembly comprising a unitary hermetic housing that encloses a variable capacitor and an inductor within an interior chamber of the housing, wherein the variable capacitor and inductor is configured to emit a return signal when subjected to a burst of RF energy;
   an external electronics assembly further comprising:
   a frequency source configured to transmit a transmission signal;
   a transmit coil coupled to the frequency source;
   a bounce back circuit coupled to the frequency source and the transmit coil, and
   a directional coupler coupled to the transmit coil and having first and second outputs, wherein the directional coupler is configured to isolate the transmission signal from the return signal.

2. The system of claim 1, further comprising:
   a voltage controlled oscillator;
   a prescaler;
   wherein the first output of the directional coupler is coupled to the voltage controlled oscillator and to a prescaler.

3. The system recited in claim 1, wherein the external electronics assembly has the size and shape of a wrist watch.

4. The system recited in claim 1, wherein the external electronics assembly is disposed on a wrist of the patient.

5. The system of claim 2, further comprising a microcontroller, and wherein the prescaler has an output coupled to an input of the microcontroller.

6. The system recited in claim 5, wherein the microcontroller is coupled to a liquid crystal display used to display the blood pressure of the patient.

7. The system recited in claim 5, wherein the external electronics assembly further comprises:
   a timekeeping chip coupled to the microcontroller; and
   a barometric pressure integrated circuit coupled to the timekeeping chip and the microcontroller that compensates blood pressure readings based upon atmospheric pressure.

8. The system of claim 5, wherein a digital-to-analog (D/A) output of the microcontroller is coupled to an analog input of the voltage controlled oscillator.

9. The system of claim 1; wherein the second output of the directional coupler is coupled to the bounce back circuit.

10. The system of claim 1, wherein, when the frequency source is varied, and when the frequency corresponds to the resonant frequency of the sensor, energy bounces back from the transmit coil to the bounce back circuit and is detected and processed to output the blood pressure of the patient.

11. The system of claim 1, wherein the frequency source comprises a direct digital synthesizer.

12. The system of claim 1, wherein the transmit coil is energized by the frequency source.

13. The system of claim 12, further comprising a microcontroller having a frequency counter, wherein the frequency source comprises a voltage controlled oscillator coupled to and controlled by the microcontroller.

14. The system of claim 13, wherein an analog sweep voltage from a digital-to-analog (D/A) output of the microcontroller drives an analog frequency control input of the voltage controlled oscillator to energize the transmit coil with pulses of differing frequency.

15. The system of claim 1, wherein the frequency source is configured to vary a frequency across a predetermined range.

16. The system of claim 1, wherein the frequency source continuously sweeps across the predetermined range of frequencies.

17. The system of claim 1, wherein the external electronics assembly further comprises a voltage controlled oscillator and a frequency counter.

18. The system of claim 17, wherein the external electronics assembly further comprises a microcontroller, wherein the bounce back circuit comprises an amplifier coupled to a detector, and wherein an output of the detector is coupled to an analog input of the microcontroller.

19. The system of claim 1, wherein the wireless monitoring electronics comprises a miniaturized one port network analyzer.

20. The system of claim 1, wherein the implantable sensor assembly is mounted within a lumen of the patient.

* * * * *